United States Patent
Orban et al.

(10) Patent No.: US 11,040,093 B2
(45) Date of Patent: Jun. 22, 2021

(54) IMMUNOMODULATORY THERAPY FOR TYPE 1 DIABETES MELLITUS AUTOIMMUNITY

(71) Applicants: Tihamer Orban, London (GB); Jalahej Heyman, London (GB); Nara Daubeney, London (GB); Piers Daubeney, London (GB)

(72) Inventors: Tihamer Orban, London (GB); Jalahej Heyman, London (GB); Nara Daubeney, London (GB); Piers Daubeney, London (GB)

(73) Assignee: Phaim Pharma Ltd, London (GB)

( * ) Notice: Subject to any disclaimer, the term of this patent is extended or adjusted under 35 U.S.C. 154(b) by 390 days.

(21) Appl. No.: 15/121,273

(22) PCT Filed: Feb. 20, 2015

(86) PCT No.: PCT/GB2015/050493
§ 371 (c)(1),
(2) Date: Aug. 24, 2016

(87) PCT Pub. No.: WO2015/128617
PCT Pub. Date: Sep. 3, 2015

(65) Prior Publication Data
US 2016/0361397 A1   Dec. 15, 2016

(30) Foreign Application Priority Data

Feb. 25, 2014 (GB) ..................... 1403258

(51) Int. Cl.
| | | |
|---|---|---|
| *A61K 38/28* | (2006.01) | |
| *A61K 39/00* | (2006.01) | |
| *C07K 14/62* | (2006.01) | |
| *C07K 14/47* | (2006.01) | |
| *G01N 33/68* | (2006.01) | |
| *A61K 45/06* | (2006.01) | |
| *C07K 14/00* | (2006.01) | |

(52) U.S. Cl.
CPC .......... *A61K 39/0005* (2013.01); *A61K 38/28* (2013.01); *A61K 45/06* (2013.01); *C07K 14/001* (2013.01); *C07K 14/4713* (2013.01); *C07K 14/62* (2013.01); *G01N 33/6893* (2013.01); *A61K 2039/55* (2013.01); *A61K 2039/55505* (2013.01); *A61K 2039/55511* (2013.01); *A61K 2039/55566* (2013.01); *A61K 2039/55588* (2013.01); *A61K 2039/57* (2013.01); *G01N 2800/42* (2013.01)

(58) Field of Classification Search
None
See application file for complete search history.

(56) References Cited

U.S. PATENT DOCUMENTS

| | | | |
|---|---|---|---|
| 5,434,131 A | 7/1995 | Linsley et al. | |
| 5,547,669 A * | 8/1996 | Rogers | C07K 14/415 424/185.1 |
| 5,814,321 A | 9/1998 | Miyahara et al. | |
| 5,844,095 A | 12/1998 | Linsley et al. | |
| 5,851,795 A | 12/1998 | Linsley et al. | |
| 5,976,538 A | 11/1999 | Hilgers et al. | |
| 6,110,746 A | 8/2000 | Cohen et al. | |
| 6,235,282 B1 | 5/2001 | Riviere et al. | |
| 6,299,884 B1 | 10/2001 | Van Nest et al. | |
| 6,797,269 B2 | 9/2004 | Mosca | |
| 7,041,634 B2 | 5/2006 | Weber et al. | |
| 7,304,033 B2 | 12/2007 | Larsen et al. | |
| 7,455,835 B2 | 11/2008 | Cohen et al. | |
| 8,497,247 B2 | 7/2013 | Cohen | |
| 8,652,488 B2 | 2/2014 | Orban | |
| 8,735,359 B2 | 5/2014 | Orban | |
| 2002/0114814 A1 | 8/2002 | Gray et al. | |
| 2003/0022836 A1 | 1/2003 | Larsen et al. | |
| 2003/0045467 A1 | 3/2003 | Orban | |
| 2003/0190323 A1 | 10/2003 | Cohen et al. | |
| 2004/0136998 A1 | 7/2004 | Bander | |
| 2004/0151725 A1 | 8/2004 | Gray et al. | |
| 2004/0202650 A1 | 10/2004 | Gribben et al. | |
| 2006/0183670 A1 | 8/2006 | Orban | |
| 2008/0019999 A1 | 1/2008 | Vratsanos et al. | |
| 2008/0160022 A1 | 7/2008 | Larsen et al. | |
| 2009/0016968 A1 | 1/2009 | Wang et al. | |
| 2009/0142308 A1 | 6/2009 | Orban et al. | |
| 2009/0246212 A1 | 10/2009 | Koshiba et al. | |
| 2011/0250225 A1 | 10/2011 | Fotin-Mleczek et al. | |

(Continued)

FOREIGN PATENT DOCUMENTS

| | | |
|---|---|---|
| EP | 1248802 | 7/2004 |
| WO | WO 1996/001846 | 1/1996 |

(Continued)

OTHER PUBLICATIONS

[No Author Listed] American Diabetes Assoc. Diabetes Care 2011;34(Suppl 1):S11-61. [No Author Listed] Diabetes Control and Complications Trial Research Group. N Engl J Med 1993;329:977-86.

[No Author Listed] DMX4001, Vaccine for Type 1 Diabetes.

[No Author Listed] IFA. Vaccine Adjuvant: Incomplete Freund's adjuvant. InvivoGen, 2011-2016, 2 pages. Retrieved from <http://www.invivogen.com/ifa> on Aug. 25, 2017.

(Continued)

*Primary Examiner* — G. R. Ewoldt
(74) *Attorney, Agent, or Firm* — Womble Bond Dickinson (US) LLP

(57) ABSTRACT

A composition for treating type 1 diabetes mellitus autoimmunity can include a therapeutically effective amount of two or more overlapping fragments of preproinsulin and a pharmaceutically acceptable carrier, wherein at least one of the polypeptide fragments is antigenic.

11 Claims, 1 Drawing Sheet

Specification includes a Sequence Listing.

(56) References Cited

U.S. PATENT DOCUMENTS

| | | |
|---|---|---|
| 2011/0311529 A1 | 12/2011 | Cohen et al. |
| 2012/0258094 A1 | 10/2012 | Cohen et al. |
| 2013/0315904 A1 | 11/2013 | Orban |
| 2013/0316375 A1 | 11/2013 | Orban |
| 2014/0099306 A1 | 4/2014 | Orban |
| 2015/0104451 A1 | 4/2015 | Orban |
| 2016/0299128 A1 | 10/2016 | Orban |
| 2016/0361397 A1 | 12/2016 | Orban et al. |

FOREIGN PATENT DOCUMENTS

| | | | |
|---|---|---|---|
| WO | WO 1999/49734 | 10/1999 | |
| WO | WO 2002/053106 | 7/2002 | |
| WO | WO 2003/035678 | 5/2003 | |
| WO | WO 2008/145998 | 12/2008 | |
| WO | W) 2009/004315 | * 1/2009 | ............ C07K 14/62 |
| WO | WO 2009/004315 | 1/2009 | |
| WO | WO 2009/029847 | 3/2009 | |
| WO | WO 2009/120341 | 10/2009 | |
| WO | WO 2012/001647 | 1/2012 | |
| WO | WO 2012/015903 | 2/2012 | |
| WO | WO 2014/004866 | 1/2014 | |

OTHER PUBLICATIONS

[No Author Listed] NCT00505375, ClinicalTrials.gov, updated Jan. 31, 2011, 4 pages.
[No Author Listed] New Hope for Immune Therapy for Children and Young Adults With Type 1 Diabetes: Founder of Orban Biotech's Landmark Findings for Abatacept Published in The Lancet. MarketWired, Aug. 5, 2011,2 pages.
Aanstoot et al., "Identification and Characterization of Glima 38, a Glycosylated Islet Cell Membrane Antigen, Which Together With GAD65 and IA2 Marks the Early Phases of Autoimmune Response in Type 1 Diabetes", J Clin Invest,Jun. 15, 1996;97(12):2772-83.
Abrams et al., "CTLA4Ig-mediated Blockade of T-cell Costimulation in Patients With Psoriasis Vulgaris", J Clin Invest 1999;103:1243-52.
Agresti, Categorical Data Analysis. New York, New York. John Wiley and Sons. 1990;Chapter 3:36-78.
Alcalde et al., "Cloning of Candidate Autoantigen Carboxypeptidase H From a Human Islet Library: Sequence Identity With Human Brain CPH", J Autoimmun 1996;9(4):525-8.
Allison et al., "Immunological Adjuvants: Desirable Properties and Side-Effects", Mol Immunol 1991;28:279-84.
Aly et al., "Immunotherapeutic Approaches to Prevent, Ameliorate, and Cure Type 1 Diabetes", Am J Therapeutics 2005; 12: 481-490.
Arai et al., "Administration of a determinant of preproinsulin can induce regulatory T cells and suppress anti-islet autoimmunity in NOD mice", Clin Immun, Jul. 1, 2010; 136(1):74-82 Abstract only.
Beebe et al., "Long-term Mortality Follow-Up of Army Recruits Who Received Adjuvant Influenza Virus Vaccine in 1951-1953", Am J Epidemiol 1972;95(4):337-46.
Bingley et al., "Combined Analysis of Autoantibodies Improves Prediction of IDDM in Islet Cell Antibody-Positive Relatives", Diabetes 1994;43:1304-10.
Blazar et al., "Infusion of anti-B7.1 (COBO) and anti-B7.2 (CD86) monoclonal antibodies inhibits murine graft-versus-host disease lethality in part via direct effects on CD4+ and CD8+ T cells", J Immunol. Oct. 15, 1996;157(8):3250-9.
Bluestone et al., "CTLA4Ig: Bridging the Basic Immunology With Clinical Application", Immunity 2006;24:233-8.
Boitard et al., "Peripherin: An Islet Antigen That Is Cross-Reactive With Nonobese Diabetic Mouse Class II Gene Products", Proc Natl Acad Sci USA 1992;89(1):172-6.
Chatenoud et al., "Clinical immunologic interventions for the treatment of type 1 diabetes", Cold Spring Harb Perspect Med. Aug. 1, 2012;2(8). pii: a007716. doi: 10.1101/cshperspect.a007716. 19 pages.

Chatenoud et al., "Clinical Immunologic Interventions for the Treatment of Type 1 Diabetes", Cold Spring Harb. Perspect. Med., Jun. 7, 2012; 2:a007716, 18 pages.
Chittasupho et al., "Autoimmune Therapies Targeting Costimulation and Emerging Trends in Multivalent Therapeutics", Ther. Deliv. 2011, 2: 873-889.
Christgau et al., "Pancreatic Beta Cells Express Two Autoantigenic Forms of Glutamic Acid Decarboxylase, a 65-kDa Hydrophilic Form and a 64-kDa Amphiphilic Form Which Can Be Both Membrane-Bound and Soluble", J Biol Chem 1991;266(31):21257-64.
Congia et al., "T-cell epitopes of insulin defined in HLA-DR4 transgenic mice are derived from preproinsulin and proinsulin" Proc Natl Acad Sci USA, Mar. 31, 1998;95(7):3833-3838.
Coppieters et al., "Trials in type 1 diabetes: Antigen-specific therapies", Clin Immunol, Dec. 2013;149(3):345-55. doi: 10.1016/j.clim. 2013.02.002.
Dotta et al., "Autoimmunity to the GM2-1 Islet Ganglioside Before and at the Onset of Type I Diabetes", Diabetes Sep. 1996;45(9):1193-6 Abstract only.
Driessens et al., "Costimulatory and Coinhibitory Receptors in Anti-Tumor Immunity", Immunol. Rev. 2009, 229: 126-144.
Genant et al., "Abatacept Inhibits Progression of Structural Damage in Rheumatoid Arthritis: Results From the Long-Term Extension of the AIM Trial", Ann Rheum Dis 2008; 67:1084-9.
Glinka et al., "Protective regulatory T cell generation in autoimmune diabetes by DNA covaccination with islet antigens and a selective CTLA-4 ligand", Mal Ther. Oct. 2006;14(4):578-87. Epub Jun. 21, 2006.
Guy, B., "The perfect mix: recent progress in adjuvant research", Nat Rev Microbiol. Jul. 2007;5(7):505-17.
Halbout et al., "T cell response to preproinsulin I and II in the nonobese diabetic mouse", J Immunol, Sep. 1, 2002;169(5):2436-43. doi: 10.4049/jimmunol.169.5.2436.
Huurman et al., "Differential inhibition of autoreactive memory- and alloreactive naive T cell responses by soluble cytotoxic T lymphocyte antigen 4 (sCTLA4), CTLA4Ig and; LEA29Y", Clin Exp Immunol. Dec. 2007;150(3):487-93. Epub Oct. 9, 2007.
Jackson, L.R., et al., "Institutional Policies and Guidelines on Adjuvants and Antibody Production", Ilar J 1995;37(3):141-152.
Janeway, C.A., et al. Immunobiology (6th ed.), 2005, p. 452, Figure 10.35.
Jiang et al., "Overlapping synthetic peptides as vaccines", Vaccine, Sep. 11, 2006;24(37-39):6356-65. doi: 10.1016/j.vaccine.2006.04. 070. Epub Jun. 5, 2006.
Kanegane, H., et al., "Expression of L-selectin (CD62L) discriminates Th1- and Th2-like cytokine-producing memory CD4+ T cells", Immunology Feb. 1996;87(2):186-90.
Kasimiotis et al., "Sex-determining Region Y-related Protein SOX13 Is a Diabetes Autoantigen Expressed in Pancreatic Islets", Diabetes 2000;49(4):555-61.
Lan et al., "Discrete Sequential Boundaries for Clinical Trials", Biometrika 1983;70:659-63.
Lenschow et al., "Differential Effects of anti-B7-1 and anti-B7-2 Monoclonal Antibody Treatment on the Development of Diabetes in the Nonobese Diabetic Mouse", J Exp Med 1995;181:1145-55.
Liping et al., "Expression of GAD65 and Islet Cell Antibody (ICA512) Autoantibodies Among Cytoplasmic ICA+ Relatives Is Associated With Eligibility for the Diabetes Prevention Trial—Type 1", Diabetes Aug. 2001;50(8):1735-40.
Lo et al., "Selective Targeting of Human Alloresponsive CD8+ Effector Memory T Cells Based on CD2 Expression", Am J Transplant 2011;11:22-3.
Matteucci, E., et al., "Altered proportions of naive, central memory and terminally differentiated central memory subsets among CD4+ and COB + T cells expressing CD26 in patients with type 1 diabetes", J Clin Immunol. Dec. 2011;31(6):977-84. doi: 10.1007/s10875-011-9573-z. Epub Sep. 2, 2011.
McDevitt, H., "Specific antigen vaccination to treat autoimmune disease", Proc Natl Acad Sci USA Oct. 5, 2004;101 Suppl 2:14627-30. Epub Oct. 4, 2004.

(56) References Cited

OTHER PUBLICATIONS

Mease et al., "Abatacept in the Treatment of Patients With Psoriatic Arthritis: Results of a Six-Month, Multicenter, Randomized, Double-Blind, Placebo-Controlled, Phase II Trial", Arthritis Rheum 2011;63:939-48.

Mehling, M., et al., "FTY720 therapy exerts differential effects on T cell subsets in multiple sclerosis", Neurology:Oct. 14, 2008;71(16):1261-7. doi: 10.1212/01.wnl.0000327609.57688.ea.

Mueller, M., et al., "Tumor eradication by immunotherapy with biodegradable PLGA microspheres—an alternative to Incomplete Freund's adjuvant", Int J Cancer Jul. 15, 2011;129(2):407-16. doi: 10.1002/ijc.25914. Epub Mar. 28, 2011.

Muir et al., "Insulin Immunization of Nonobese Diabetic Mice Induces a Protective Insulitis Characterized by Diminished Intraislet Interferon-Gamma Transcription", J Clin Invest 1995;95:628-34.

Orban et al., "Autoantigen-specific Regulatory T Cells Induced in Patients With Type 1 Diabetes Mellitus by Insulin B-chain Immunotherapy", J Autoimmun Jun. 2010;34(4):408-15. doi: 10.1016/j.jaut.2009.10.005.

Orban et al., "Co-stimulation Modulation With Abatacept in Patients With Recent-Onset Type 1 Diabetes: A Randomised, Double-Blind, Placebo-Controlled Trial",Lancet 2011;378(9789):412-9.

Orban, T., et al., "Prevention of Type 1 Diabetes Mellitus using a Novel Vaccine", Ther Adv Endocrinol Metab Feb. 2011;2(1):9-16 doi: 10.1177/2042018810390546.

Orban, T., et al., "Reduction in CD4 central memory T-cell subset in costimulation modulator abatacept-treated patients with recent—Onset type 1 diabetes is associated with slower C-peptide decline", Diabetes. Oct. 2014;63(10):3449-57. doi: 10.2337/db14-0047. Epub May 16, 2014.

Palmer et al., "C-peptide is the appropriate outcome measure for type 1 diabetes clinical trials to preserve beta-cell function: report of an ADA workshop", Oct. 21-22, 2001 Diabetes Jan. 2004;53(1):250-64.

Phillips et al., Current state of type 1 diabetes immunotherapy: incremental advances, huge leaps, or more of the same? Clin Dev Immunol 2011;2011:432016. doi: 10.1155/2011/432016. Epub Jul. 18, 2011.

Pietropaolo et al, "Islet Cell Autoantigen 69 kD (ICA69). Molecular Cloning and Characterization of a Novel Diabetes-Associated Autoantigen",J Clin Invest 1993;92:359-71.

Ramiya et al., "Antigen Based Therapies to Prevent Diabetes in NOD Mice", J Autoimmun 1996;9:349-56.

Rigby, M.R., et al., "CD28/CD154 blockade prevents autoimmune diabetes by inducing nondeletional tolerance after effector I-cell inhibition and regulatory I-cell expansion", Diabetes, Oct. 1, 2008; 57(10): 2672-2683.

Roep, "The role of T-cells in the pathogenesis of Type 1 diabetes: from cause to cure", Diabetologia. Mar. 2003;46(3):305-21. Epub Mar. 22, 2003.

Sanderson et al., "Autoimmunity in a phase I trial of a fully human anti-cytotoxic T-lymphocyte antigen-4 monoclonal antibody with multiple melanoma peptides and Montanide ISA 51 for patients with resected stages III and IV melanoma", J Clin Oncol. Feb. 1, 2005;23(4):741-50. Epub Dec. 21, 2004.

Schengrund C.L., "Gangliosides: Glycosphingolipids Essential for Normal Neural Development and Function", Trends Biochem Sci. Jul. 2015; 40(7):397-406 . doi: 10.1016/j.tibs.2015.03.007. Epub May 1, 2015.

Sturmhoefel et al., "Potent Activity of Soluble B7-IgG Fusion Proteins in Therapy of Established Tumors and as Vaccine Adjuvant", Cancer Res 1999, 59:4964-4972.

Tagami et al., "Ganglioside GM3 Participates in the Pathological Conditions of Insulin Resistance", J Biol Chem Nov. 13, 2002;277(5):3085-92.

Tanbara, K., et al., "Angiogenesis therapy for ischemic cardiomyopathy. Utility of basic fibroblast growth factor sustained release system", Japanese-Language Article. English Abstract Only. History of Medicine, 1st Saturday Special Issue New Treatment Strategy for Heart Failure, New Treatment Target, 2003,206(10):824-828.

Vadasz et al., "Abnormal Deposition of Collagen Around Hepatocytes in Wilson's Disease Is Associated With Hepatocyte Specific Expression of Lysyl Oxidase and Lysyl Oxidase Like protein-2", J Hepatol., Sep. 2005;43(3):499-507, doi: 10.1016/j.jhep.2005.02.052.

Vincenti et al., "Costimulation Blockade With Belatacept in Renal Transplantation", N Engl J Med 2005;353:770-81.

Yu et al., "Expression of GAD65 and islet cell antibody (ICA512) autoantibodies among cytoplasmic ICA+ relatives is associated with eligibility for the Diabetes Prevention Trial-Type 1", Diabetes. Aug. 2001;50(8):1735-40.

Zhang et al., "Autoantibodies to IA-2 in IDDM: Location of Major Antigenic Determinants", Diabetes 1997;46:40-3 Abstract only.

Zhang, X., et al., Acute response of peripheral blood cell to autologous hematopoietic stem cell transplantation in ype 1 diabetic patient. PLoS One. 2012;7(2):e31887. doi: 10.1371/journal.pone.0031887. Epub Feb. 22, 2012.

* cited by examiner

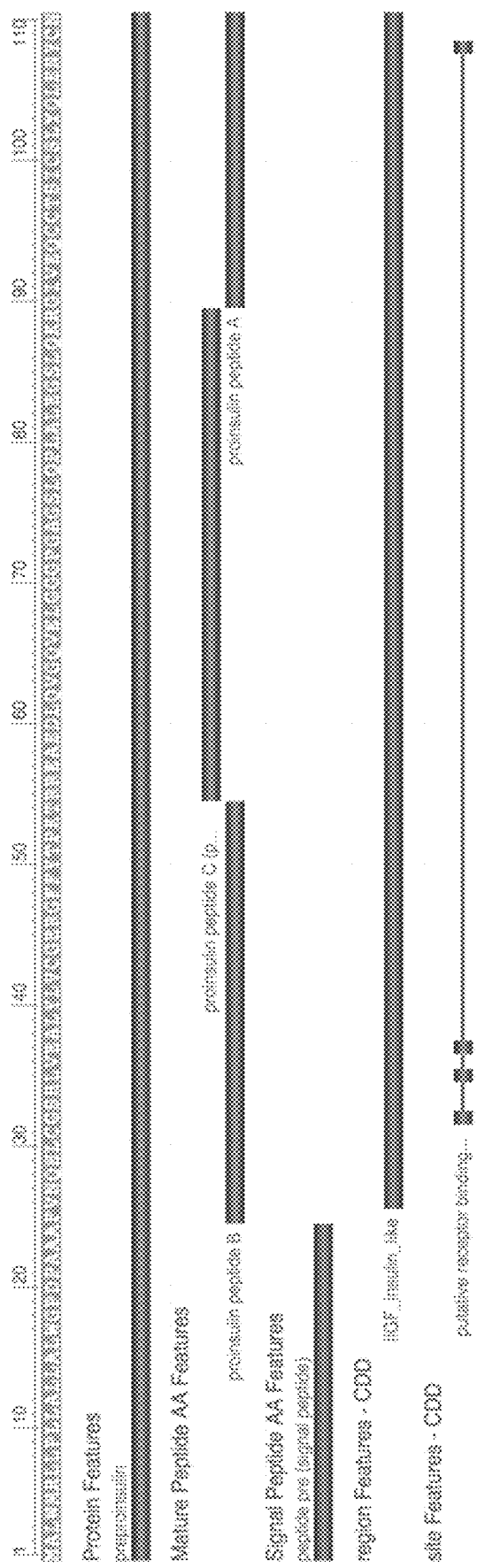

SEQUENCE LISTING

```
<160> NUMBER OF SEQ ID NOS: 1

<210> SEQ ID NO 1
<211> LENGTH: 110
<212> TYPE: PRT
<213> ORGANISM: Homo sapiens

<400> SEQUENCE: 1

Met Ala Leu Trp Met Arg Leu Leu Pro Leu Leu Ala Leu Leu Ala Leu
1               5                   10                  15

Trp Gly Pro Asp Pro Ala Ala Ala Phe Val Asn Gln His Leu Cys Gly
            20                  25                  30

Ser His Leu Val Glu Ala Leu Tyr Leu Val Cys Gly Glu Arg Gly Phe
        35                  40                  45

Phe Tyr Thr Pro Lys Thr Arg Arg Glu Ala Glu Asp Leu Gln Val Gly
    50                  55                  60

Gln Val Glu Leu Gly Gly Gly Pro Gly Ala Gly Ser Leu Gln Pro Leu
65                  70                  75                  80
```

```
Ala Leu Glu Gly Ser Leu Gln Lys Arg Gly Ile Val Glu Gln Cys Cys
                85                  90                  95

Thr Ser Ile Cys Ser Leu Tyr Gln Leu Glu Asn Tyr Cys Asn
            100                 105                 110
```

IMMUNOMODULATORY THERAPY FOR TYPE 1 DIABETES MELLITUS AUTOIMMUNITY

CROSS REFERENCE TO RELATED APPLICATIONS

This application claims the benefit of Application Nos. PCT/GB2015/050493 filed on Feb. 20, 2015 and GB 1403258.5 filed on Feb. 25, 2014, the disclosures of which are all herein incorporated by reference in their entirety.

SEQUENCE LISTING

The instant application contains a Sequence Listing which has been submitted electronically in ASCII format and is hereby incorporated by reference in its entirety. Said ASCII copy, created on Apr. 1, 2019, is named SUBS_SEQL.txt and is 1,439 bytes in size.

FIELD OF THE INVENTION

The present invention relates generally to the field of autoimmune disease and specifically to the treatment, prevention, or delayed progression of Type 1 diabetes mellitus. The present invention relates more particularly to immunomodulatory therapy for type 1 diabetes mellitus autoimmunity.

BACKGROUND OF THE INVENTION

The onset of human Type 1 diabetes mellitus ("T1DM") is the clinical manifestation of β-cell failure caused by T cell mediated autoimmune destruction. T1DM results in a life-long dependence on daily insulin injections and exposure to both the acute and late complications. Despite the significant progress that has been made in its treatment, T1DM represents a severe burden on the individual and on society. T1DM is a particular burden to children and their families, representing one of the most severe, chronic childhood diseases. While the onset of T1DM can occur in adulthood, it is largely a problem in children and youngsters. There is a bimodal peak age of T1DM onset, between ages 4-7 and ages 14-16 years. The worldwide incidence of T1DM is increasing, with the greatest increase in children under the age of 5 years. Therefore, there is an urgent and growing need to ameliorate this disease.

T1DM is a common endocrine disease in children, and up to 80% of children with T1DM present with diabetic ketoacidosis (DKA), which is associated with both short-term risks and long-term consequences. Short-term, and often life threatening, complications include hypo and hyperglycemic episodes often complicated with acidosis. Long-term complications can represent further significant morbidity and mortality. Patients may face both macro and microvascular complications, cardiovascular complications, hypertension, retinopathy, nephropathy, and neuropathy, which can be debilitating and life threatening. These can be reduced with improved care but currently cannot be eliminated in T1DM patients. Further sever complications include kidney failure, blindness, and amputation.

SUMMARY OF THE INVENTION

The present invention, in various aspects and embodiments, provides immunomodulatory therapy for type 1 diabetes mellitus ("T1DM"), including therapeutics, therapies, diagnostics, kits, and methods for making the same.

For example, the invention provides compositions comprising a therapeutically effective amount of two or more overlapping fragments of SEQ ID NO:1 (i.e., preproinsulin) and a pharmaceutically acceptable carrier, wherein at least one of the polypeptide fragments is antigenic. The compositions can be for treating type 1 diabetes mellitus. In addition to being immunomodulatory (e.g., as opposed to immunosuppressive) certain therapeutics in accordance with the present invention are not metabolically active (e.g., without insulin-like activity) and are thus advantageously safe for use (i.e., a large dose would not kill or harm a patient, as would a large dose of insulin).

In addition to mitigating clinical T1DM, the invention can, in certain embodiments, prevent the development or progression of pre-clinical T1DM. This can be advantageous because, in various aspects and embodiments, it can delay the clinical onset of T1DM, thus provide longer symptom free period, or prevent the clinical onset of T1DM altogether. At the time of diagnosis, a T1DM patient may still have appreciable amounts of insulin production (e.g., functioning beta cells as measured by C-peptide levels). An intervention that can stop or delay the loss of functional residual β-cell mass in T1DM is highly desirable because it may provide longer 'remission' period after the onset of T1DM. Furthermore, the present invention may reduce or delay development of acute and chronic complications in certain patients.

Similarly, the present invention may significantly improve the day-to-day management for subjects with diabetes. For example, the present invention may provide protection against hypoglycemia and provide improved metabolic control, resulting in a delay and/or reduction in the micro and macro-vascular complications of diabetes. In summary, preservation of residual beta cell function by the present invention is highly desirable as it may lead to reduction of the short- and long-term complications of T1DM.

In one aspect, the invention provides a composition including a therapeutically effective amount of two or more overlapping fragments of SEQ ID NO:1 (i.e., preproinsulin) and a pharmaceutically acceptable carrier, wherein at least one of the polypeptide fragments is antigenic. In various embodiments, the composition is for treating type 1 diabetes mellitus. In another aspect, the invention provides a composition comprising a therapeutically effective amount of two or more overlapping fragments of SEQ ID NO:1 and a pharmaceutically acceptable carrier, wherein at least one of the polypeptide fragments is antigenic, for use in treating type 1 diabetes mellitus autoimmunity.

In another aspect, the invention provides treatment for type 1 diabetes mellitus including administering a therapeutically effective amount of the composition of any one of the compositions in accordance with the present invention to a subject in need thereof.

In another aspect, the invention provides a treatment for type 1 diabetes mellitus including (i) selecting a subject in need of a treatment for type 1 diabetes mellitus autoimmunity; and (ii) administering a therapeutically effective amount of the composition of any one of the compositions in accordance with the present invention to the subject.

In another aspect, the invention provides a kit for treating type 1 diabetes mellitus autoimmunity including (i) therapeutically effective amount of the composition of any one of the compositions in accordance with the present invention; and (ii) instructions for administration of the composition to a subject in need thereof.

In another aspect, the invention provides a kit for diagnosing and treating type 1 diabetes mellitus autoimmunity including (i) a type 1 diabetes mellitus autoimmunity diagnostic (e.g., autoantibody testing—anti-insulin IAA, anti GAD65, anti IA2—insulinoma antigen 2, anti Zn8—zink transporter 8 antibodies, T cell biomarkers and the like); (ii) a therapeutically effective amount of the composition of any one of claims 1-21; and (iii) instructions for diagnosing a subject and administering the composition to the subject if the subject is in need thereof.

In another aspect, the invention provides a method of making a composition in accordance with the present invention for treating type 1 diabetes mellitus described herein including combining a two or more overlapping fragments of SEQ ID NO:1 and a pharmaceutically acceptable carrier, wherein at least one of the polypeptide fragments is antigenic.

In various embodiments of the present invention, any of the aspects above can be combined with any one or more features below.

In various embodiments, the fragments are about 20 amino acids in length.

In various embodiments, the fragments are about 30, 29, 28, 27, 26, 25, 24, 23, 22, 21, 20, 19, 18, 17, 16, 15, 14, 13, 12, 11, 10, 9 and/or 8 amino acids in length. Composition in accordance with the present invention can include fragments of uniform length (e.g., all about 20 amino acids in length) as well as distributions of lengths.

In various embodiments, the fragments include a first polypeptide fragment and a second polypeptide fragment that overlap by about 10 amino acids.

In various embodiments, the fragments include a first polypeptide fragment and a second polypeptide fragment that overlap by about 20, 19, 18, 17, 16, 15, 14, 13, 12, 11, 10, 9, 8, 7, 6, 5, 4, or 3 amino acids. Composition in accordance with the present invention can include fragments of uniform overlap (e.g., all about 10 amino acids) as well as varying overlap.

In various embodiments, the fragments are about 20 amino acids in length and include a first polypeptide fragment and a second polypeptide fragment that overlap by about 10 amino acids. Alternatively, the fragments are about 20 amino acids in length and comprise a first polypeptide fragment and a second polypeptide fragment that overlap by about 20, 19, 18, 17, 16, 15, 14, 13, 12, 11, 10, 9, 8, 7, 6, 5, 4, or 3 amino acids.

In various embodiments, the fragments, first polypeptide fragment and/or second polypeptide include 3, 4, 5, 6, 7, 8, 9, 10, 15, 20, 25, 30, 35, 40, 45, 50, 60, 70, 80, 90, 100 or more overlapping preproinsulin polypeptide fragments. Compositions can include fragments essentially covering the entire preproinsulin sequence, or may be limited to a set or subset of preproinsulin epitopes. Composition can include the entire preproinsulin sequence (e.g., 110 amino acids), covered by a predetermined set of fragments (e.g., one hundred fragment that are each 10 amino acid long).

In various embodiments, the fragments include at least one internal preproinsulin epitope. The fragments can include two or more preproinsulin epitopes.

In various embodiments, the fragments do not exhibit insulin-like metabolically activity.

In various embodiments, the fragments comprise at least one epitope that is not present in insulin.

In various embodiments, each of the two or more overlapping fragments comprises a preproinsulin epitope. Epitopes can include known epitopes, for example B chain B9-23 and A chain 1-15. Epitopes can include cryptic epitopes, which are exposed as a result of fragmenting preproinsulin (i.e., epitpoes that are not solvent accessible in native, folded preproinsulin). Epitopes can include the full set of epitopes present in the preproinsulin sequence (or analog thereof). Epitopes can include one or more epitopes that are unique to beta cells (i.e., the specific target of autoimmunity in T1DM).

In various embodiments, the composition includes an adjuvant that promotes regulatory immune response.

In various embodiments, the composition includes an adjuvant that includes an oil and an emulsifier mixed with water.

In various embodiments, the composition includes an incomplete Freund's adjuvant (IFA).

In various embodiments, the composition includes an alum adjuvant. In various embodiments, the composition includes an adjuvant such as squalene, killed bacteria and toxoids, aluminum salts-alum/inorganic compounds, liposomes, nanoemulsions, dendrimers, and the like.

In various embodiments, the composition is immunomodulatory.

In various embodiments, the composition is not immunosupressive.

In various embodiments, the composition elicits a Th2 immune response.

In various embodiments, the composition does not elicit a Th1 immune response.

In various embodiments, the composition further includes one or more additional therapeutics (e.g., a second therapeutic of T1DM). Examples of additional therapeutics include proregulatory leucotrines, cytokines (e.g., IL-10, TGF beta, and the like), and/or other substances for promoting or enhancing regulatory responses, or restoring self-tolerance. Other examples of additional therapeutics include anti-inflammatory leukotrines and cytokines (e.g., an IL-1 antagonist) that block autoimmune responses. In various embodiments, the composition further comprises one or more beta cell promoting agents, anti-inflammatory agents, and/or anti-autoimmunity agents. Alternatively, the one or more additional therapeutics can be separate to the composition, In these embodiments, the one or more additional therapeutics can be administered in combination with the composition and/or separately to the composition. The one or more additional therapeutics can be administered concurrently with the composition; and/or administered prior to and/or subsequent to the administration of the composition. For example, one or more additional therapeutics may form part of the composition, and administered with one or more additional therapeutics, separate to the composition, either concurrently, prior to or subsequent to the composition.

In various embodiments, the subject is a human adult. In another embodiment, the subject is a human juvenile.

In various embodiments, the subject has type 1 diabetes mellitus and the treatment achieves at least one clinical endpoint (e.g., improved C-peptide secretion, reduced insulin use, improved HbA1c, and the like).

In various embodiments, the subject has type 1 diabetes mellitus and the treatment mitigates at least one symptom of the type 1 diabetes mellitus (e.g., frequency of hypoglyceamias/hyperglyceamias, reduced glucosuria, level/number of hospitalization, and level/number of complications such as nephropathy, neuropathy, and retinopathy).

In various embodiments, the subject has pre-clinical type 1 diabetes mellitus and the treatment prevents or delay progression to clinical type 1 diabetes mellitus.

In various embodiments, the subject is predisposed to developing type 1 diabetes mellitus and the treatment prevents or delays development of type 1 diabetes mellitus.

In various embodiments, the treatment mitigates autoimmunity to pancreatic beta cells.

In various embodiments, the administering step comprises intravenous, intramuscular, or subcutaneous administration.

In various embodiments, the method also includes administering one or more additional therapeutics (e.g., a second therapeutic of T1DM). Examples of additional therapeutics include agents promoting beta cell regeneration and/or growth (e.g., Exenatide) and/or other anti-inflammatory/anti-autoimmunity agents (e.g., Vitamin D and its analogs). In various embodiments, the composition further comprises one or more beta cell promoting agents, anti-inflammatory agents, and/or anti-autoimmunity agents. Alternatively, the one or more additional therapeutics can be separate to the composition, In these embodiments, the one or more additional therapeutics can be administered in combination with the composition and/or separately to the composition. The one or more additional therapeutics can be administered concurrently with the composition; and/or administered prior to and/or subsequent to the administration of the composition. For example, one or more additional therapeutics may form part of the composition, and administered with one or more additional therapeutics, separate to the composition, either concurrently, prior to or subsequent to the composition.

In various embodiments, the method also includes determining if a subject is in need of a treatment for type 1 diabetes mellitus autoimmunity prior to administering the therapeutically effective amount of a therapeutic compound or composition in accordance with the present invention.

In various embodiments, a therapeutically effective amount can be 5 micrograms to 10 milligrams, 0.5 to 4.0 milligrams, or any value there between. In various embodiments, a therapeutically effective amount can be 5, 10, 25, 50, 75, 100, 125, 150, 175, 200, 225, 250, 275, 300, 350, 400, 450, 500, 600, 700, 800, or 900 micrograms, or any value there between. In various embodiments, a therapeutically effective amount can be 1.0, 1.25, 1.5, 1.75, 2.0, 2.25, 2.5, 2.75, 3.0, 3.25, 3.5, 3.75, 4.0, 4.25, 4.5, 4.75, 5.0, 5.5, 6.0, 6.5, 7.0, 7.5, 8.0, 8.5, 9.0, 9.5, or 10 milligrams, or any value there between.

In various embodiments, administration can include a depot injection. Administration can be in repeated intervals of about 6 months to 2 years. In various embodiments, the interval can be 1, 2, 3, 4, 5, 6, 7, 8, 9, 10, or 11 months, or 1, 2, 3, 4 years. In various embodiments, the interval can be quarterly, semi annually, or annually. In various embodiments, the interval can be determined by monitoring an immune-modulatory response (e.g., Th1/regulatory cells) and adjusting the treatment accordingly (e.g., re-dose when the T cell number/activity start to fall).

BRIEF DESCRIPTION OF THE DRAWINGS

A detailed description of various embodiments is provided herein below with reference, by way of example, to the following drawings. The skilled person in the art will understand that the drawings, described below, are for illustration purposes only. The drawings are not intended to limit the scope of the applicant's teachings in any way.

FIG. 1 is an illustration of a preproinsulin 110 amino acid peptide.

DETAILED DESCRIPTION

The present invention, in various aspects and embodiments, provides immunomodulatory therapy for type 1 diabetes mellitus ("T1DM") autoimmunity, including therapeutics, therapies, diagnostics, kits, and methods for making the same. For example, the invention provides compositions for treating type 1 diabetes mellitus autoimmunity comprising a therapeutically effective amount of two or more overlapping fragments of SEQ ID NO:1 (i.e., preproinsulin) and a pharmaceutically acceptable carrier, wherein at least one of the polypeptide fragments is antigenic.

Insulin and Preproinsulin

Insulin is synthesized in the pancreatic islets beta cells from its precursor preproinsulin. Insulin is both produced and degraded within the pancreatic beta cell. Preproinsulin is a 110 amino acid biologically inactive precursor to the biologically active endocrine hormone insulin. Preproinsulin is converted into proinsulin by signal peptidases, which remove its signal peptide from its N-terminus. Finally, proinsulin is converted into the bioactive hormone insulin by removal of its connecting peptide (C-peptide).

Almost no preproinsulin exists outside beta cells, because removal of the signal peptide is not a separate step, but rather is closely linked to translocation of the protein into the endoplasmic reticulum (ER). For the same reason, preproinsulin is rarely used medicinally, unlike insulin, the mature product, and proinsulin, a stable ER intermediate.

FIG. 1 is an illustration of a preproinsulin 110 amino acid peptide having the following sequence:

```
                                              (SEQ ID NO: 1)
MALWMRLLPLLALLALWGPDPAAAFVNQHLCGSHLVEALYLVCGERGFFY
TPKTRREAEDLQVGQVELGGGPGAGSLQPLALEGSLQKRGIVEQCCTSIC
SLYQLENYCN
```

In various aspects and embodiments, the invention contemplates not only SEQ ID NO:1, but also homologs and analogs thereof. For example, the invention can employ a preproinsulin sequence that is structurally and/or functionally homologous to SEQ ID NO:1. Homology can include 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, or 70% homology. Analogous sequences can include preproinsulin sequences from non-human species, humans having mutated preproinsulin sequences or preproinsulin sequence polymorphisms, and synthetic peptide sequences comprising one or more preproinsulin epitopes or cross-reactive epitopes.

Insulin biogenesis begins with the synthesis of preproinsulin in rough endoplasmic reticulum and conversion of preproinsulin to proinsulin. Preproinsulin is converted to proinsulin shortly after (or during) translocation into the lumen of the rough endoplasmic reticulum. Proinsulin is then transported to the trans-cisternae of the Golgi complex where it is directed towards nascent, immature secretory granules. Conversion of proinsulin to insulin and C-peptide by proteolytic cleavage arises within secretory granules, and is dependent upon their acidification via ATP-dependent proton pump. The proinsulin consists of B-chain, C-peptide and A chain. C-peptide is cut out and the two ends B-chain and A chain connected by disulphide bonds form the insulin. The secretory granules undergo a maturation process in which insulin content becomes crystallized with zinc and calcium as dense-core granules. These new mature dense-core insulin granules form two distinct intracellular pools, the readily releasable pools (RRP) and the reserved pool. These two populations of dense-core granules may be responsible for the biphasic nature of insulin release. The RRP granules are associated with the plasma membrane and undergo an acute calcium-dependent release responsible for first phase insulin secretion. These granule contents are discharged by exocytosis in response to an appropriate stimulus primarily glucose. This process represents the regulated secretory pathway to which more than 99% of proinsulin is directed in beta cells of a healthy individual. In contrast, second phase insulin secretion requires the trafficking of the reserved granule pool to the plasma membrane, and involves the rapid transfer of products from the Golgi complex to the plasma membrane for immediate release. The initial trigger for insulin granule fusion with the plasma membrane is a rise in intracellular calcium and in the case of glucose stimulation results from increased production of ATP, closure of the ATP-sensitive potassium channel and cellular depolarization. In turn, this opens voltage-dependent calcium channels allowing increased influx of extracellular calcium. Calcium may bind to members of the fusion regulatory proteins synaptogamin that functionally represses the fusion inhibitory protein complex.

In brief, preproinsulin is a beta cell specific antigen and thus can form the basis of the immunomodulaory compositions and therapies for T1DM in accordance with the present invention.

Preproinsulin Fragments

The present invention, in various embodiments, utilizes preproinsulin by breaking it up into metabolically inactive overlapping preproinsulin polypeptide fragments, to capture preproinsulin's immune modulatory potentials as a beta cell restricted antigen. By breaking preproinsulin up into overlapping peptides, the immune system can be presented with peptide sequences which are unique to the preproinsulin, but that are not present either in the insulin or in the C-peptides (both of which are present in circulation).

In various embodiments, the present invention utilizes preproinsulin fragments in immunomodulatory compositions. The fragments can be about 20 amino acids in length. Alternatively, fragments can be another length or lengths, for example the fragments can be about 30, 29, 28, 27, 26, 25, 24, 23, 22, 21, 20, 19, 18, 17, 16, 15, 14, 13, 12, 11, 10, 9 and/or 8 amino acids in length. Composition in accordance with the present invention can include fragments of uniform length (e.g., all about 20 amino acids in length) as well as distributions of lengths. Fragment lengths, or distributions thereof, can be selected to optimize an immunomodulatory effect.

In various embodiments, the fragments include a first polypeptide fragment and a second polypeptide fragment that overlap by about 10 amino acids. Alternatively, the fragments can include a first polypeptide fragment and a second polypeptide fragment that overlap by about 20, 19, 18, 17, 16, 15, 14, 13, 12, 11, 10, 9, 8, 7, 6, 5, 4, or 3 amino acids. Composition in accordance with the present invention can include fragments of uniform overlap (e.g., all about 10 amino acids) as well as varying overlap. Again, overlap lengths, or distributions thereof, can be selected to optimize an immunomodulatory effect.

In various embodiments, the fragments are about 20 amino acids in length and include a first polypeptide fragment and a second polypeptide fragment that overlap by about 10 amino acids. Alternatively, the fragments are about 20 amino acids in length and comprise a first polypeptide fragment and a second polypeptide fragment that overlap by about 20, 19, 18, 17, 16, 15, 14, 13, 12, 11, 10, 9, 8, 7, 6, 5, 4, or 3 amino acids.

In various embodiments, fragments, first polypeptide fragment and/or second polypeptide fragment can include 3, 4, 5, 6, 7, 8, 9, 10, 15, 20, 25, 30, 35, 40, 45, 50, 60, 70, 80, 90, 100 or more overlapping preproinsulin polypeptide fragments. Compositions can include fragments essentially covering the entire preproinsulin sequence, or may be limited to a set or subset of preproinsulin epitopes. Composition can include the entire preproinsulin sequence (e.g., 110 amino acids), covered by a predetermined set of fragments (e.g., one hundred fragment that are each 10 amino acid long).

In various embodiments, the fragments do not exhibit insulin-like metabolically active (e.g., in a human subject). Such embodiments can be advantageous because they can allow for administration of concentrations of fragments that are greater than a preferred, or maximum tolerated, dose of insulin.

In one embodiment, the fragments include at least one internal preproinsulin epitope. The fragments can include two or more preproinsulin epitopes. The epitopes can be selected to optimize an immunomodulory effect.

In various embodiments, the fragments comprise at least one epitope that is not present in insulin. Such embodiments can advantageously limit the effect of compositions in accordance with the present invention to cells including preproinsulin.

In one embodiment, each of the two or more overlapping fragments comprises a preproinsulin epitope. Epitopes can include known epitopes, for example B chain B9-23 and A chain 1-15. Epitopes can include cryptic epitopes, which are exposed as a result of fragmenting preproinsulin (i.e., epitopes that are not solvent accessible in native, folded preproinsulin). Epitopes can include the full set of epitopes present in the preproinsulin sequence (or analog thereof). Epitopes can include one or more epitopes that are unique to beta cells (i.e., the specific target of autoimmunity in T1DM).

In one embodiment, the fragments comprise one or more of the insulin A-chain 1-15 epitope, B-chain 9-23 or B-chain 11-27 epitopes, and epitopes C3-27/C13-32 and C13-29 on the C-peptide.

Without wishing to be bound by any particular theory, a loss of self-tolerance to insulin, a primary autoantigen, may unleash autoaggressive T cells and initiates autoimmunity. Thus, destruction of insulin producing cells can start well before clinical onset of T1DM. At clinical diagnosis of some subjects, there can still be about 20-50% of self-insulin production, which can be completely destroyed over few years without medical intervention. The destruction process is T cell-mediated, and may involve CD4+ cells. However, regulatory T cells (Tregs) that are capable of suppressing the autoaggressive T cell population may also play a critical role. Tregs include naturally occurring $CD4^+CD25^+$ cells and antigen-induced $CD4^+$ Th2-like regulatory cells. An imbalance between the autoaggressive and regulatory sets of T cells may be at the core of autoimmunity. Therefore, a successful interventions may be implemented by deleting the autoaggressive cells and/or boosting the regulatory population, in order to re-establish control and create a healthy balance.

Again, without wishing to be bound by any particular theory, antigen challenge in an autoimmune setting may stimulate beneficial changes in T cell subsets (e.g., Th2 vs. Th1), in cytokine production, and/or in regulatory T cells induction. In practice, antigen-specific therapeutic approaches for autoimmune diseases may use putative self-antigens that have been implicated in the disease aetiopathogenesis. Insulin, is a beta-cell specific major protein and is also moderately immunogenic when used alone. However, when insulin is used, there is a concern about hypoglycemia among other side effects. Thus insulin related peptides can be a safer choice than insulin for human use, because they do not necessarily have a hypoglycemic effect.

Prolonged peripheral presentation of self-antigens can cause low-avidity auto reactive T cells to differentiate into memory-like auto regulatory T cells that suppress both auto reactive cytotoxic T lymphocytes (CTLs) and the presentation of self-antigens, thus protecting beta cells from further damage. The autoimmune process in T1DM selectively kills the beta cells in the pancreatic islets and do not destroy other endocrine cells like glucagon producing alfa-cells. This selectivity indicates that the self-antigen, which became autoantigen is probably restricted to the beta cell. Only one peptide is uniquely present in beta cells and not in any other cells and this is the preproinsulin, the precursor of insulin. In contrast, insulin and C-peptide are secretory products, which leave the beta cells and circulate in blood.

In brief, peripheral reintroduction of the primary autoantigen, e.g., preproinsulin polypeptides in adjuvant, can induce regulatory immune response and reestablish immune tolerance in T1DM patients. If the autoimmune process can be arrested even in this late stage, beta cells can be preserved and possibly permit their regeneration. This is a unique, T1DM specific, targeted and non-immunosuppressive approach, thus particularly well suited for children and young adults with T1DM and for prevention in at risk human subjects as well.

Adjuvants

Compositions in accordance with the present invention can include an adjuvant that promotes a regulatory immune response (e.g., in a human subject). In one embodiment, the composition includes an adjuvant that includes an oil and an emulsifier mixed with water. In one embodiment, the composition includes an incomplete Freund's adjuvant (IFA). In one alternative embodiment, the composition includes an alum adjuvant or sequalene, or killed bacteria, or toxoids, or inorganic compounds, or liposomes, or dendrimers, or nanoemulsions, and the like.

An IFA (commercially available, for example, as Adjuvant Montanide ICA 51 from Seppic Inc., France) typically consists of two components, an oil and an emulsifier. IFAs can be used with antigens to elicit cell-mediated immunity and the production of antibodies of protective isotypes (IgG2a in mice and IgG1 in primates). Different types of adjuvants share similar side effects, such as a reaction at the injection site and pyrogenicity. Alum, a commonly used adjuvant for human vaccine, also may produce an appreciable granulomatous response at the injection site.

The mode of action of an incomplete Freund's adjuvant can involve non-specific as well as specific immune responses (e.g., in a human subject). IFAs can also acts as an antigen vehicle and a slow release or long-term antigen presentation device. This can be important characteristics of IFA as prolong peripheral presentation of self-antigens can cause low-avidity auto reactive T cells to differentiate into memory-like auto regulatory T cells that suppress both auto reactive CTLs and the antigen presenting cells (APCs) self-antigens presentation.

The specific enhancing effect of the IFA on the antigen immunogenicity may lead to increased humoral immunity (e.g., preferentially protective antibody production; IgG1 in humans and IgG2a in mice) and to elicit specific cell mediated immunity (e.g., Th2 type). Because of reliability and duration of protection, the use of autoantigen specific immunization therapy in T1DM can be advantageous.

Combination Therapies

Compositions in accordance with the present invention can include one or more therapeutics in addition to preproinsulin fragments. An additional therapeutic can be a therapeutic for T1DM and/or another related or coexisting condition.

Examples of additional therapeutics include proregulatory leucotrines, cytokines (e.g., IL-10, TGF beta, and the like), or other substances for promoting or enhancing regulatory responses, or restoring self-tolerance. Other examples of additional therapeutics include anti-inflammatory leukotrines and cytokines (e.g., an IL-1 antagonist) that block autoimmune responses. Further examples of additional therapeutics include agents promoting beta cell regeneration and/or growth (e.g., Exenatide) and/or other anti-inflammatory/anti-autoimmunity agents (e.g., Vitamin D and its analogs). The one or more additional therapeutics can be part of the composition; and/or the one or more additional therapeutics can be separate to the composition. The one or more additional therapeutics can be administered in combination with the composition and/or separately to the composition. The one or more additional therapeutics can be administered concurrently with the composition; and/or administered prior to and/or subsequent to the administration of the composition. For example, one or more additional therapeutics may form part of the composition, and be administered with one or more additional therapeutics, separate to the composition, either concurrently, prior to or subsequent to the composition.

Pharmaceutical Compositions and Kits

In one aspect, the invention provides a composition for treating type 1 diabetes mellitus autoimmunity including a therapeutically effective amount of two or more overlapping fragments of SEQ ID NO:1 (i.e., preproinsulin) and a pharmaceutically acceptable carrier, wherein at least one of the polypeptide fragments is antigenic.

Numerous pharmaceutically acceptable carriers are known in the art. Examples can be found, e.g., in The *Handbook of Pharmaceutical Excipients* Rowe et al. (eds.) Pharmaceutical Press; 7 Updated edition (Jun. 6, 2012). Example adjuvants include incomplete Freund's adjuvant, alum, sequalene, killed bacteria, toxoids and inorganic compounds, liposomes, lipid based nanoparticles, nanoemulsion or nanogels, or targeted drug delivery systems like dendrimers, and the like.

In another aspect, the invention provides a kit for treating type 1 diabetes mellitus autoimmunity including (i) therapeutically effective amount of the composition of any one of the compositions in accordance with the present invention; and (ii) instructions for administration of the composition to a subject in need thereof.

In another aspect, the invention provides a kit for diagnosing and treating type 1 diabetes mellitus autoimmunity including (i) a type 1 diabetes mellitus autoimmunity diagnostic (e.g., autoantibody testing—anti-insulin IAA, anti GAD65, anti IA2—insulinoma antigen 2, anti Zn8—zink transporter 8 antibodies, T cell biomarkers, and the like); (ii) a therapeutically effective amount of the composition of any one of claims 1-21; and (iii) instructions for diagnosing a subject and administering the composition to the subject if the subject is in need thereof.

Methods of Manufacture

In another aspect, the invention provides a method of making a composition in accordance with the present invention for treating type 1 diabetes mellitus autoimmunity described herein including combining a two or more overlapping fragments of SEQ ID NO:1 (or analog or homolog thereof) and a pharmaceutically acceptable carrier, wherein at least one of the polypeptide fragments is antigenic. A person skilled in the art will appreciate that the polypeptide fragments can be synthesized using known polypeptide synthetic methodologies. One illustrative example is provided in Example 1 below.

Methods of Use

In another aspect, the invention provides treatment for type 1 diabetes mellitus autoimmunity including administering a therapeutically effective amount of the composition of any one of the compositions in accordance with the present invention to a subject in need thereof.

In another aspect, the invention provides a treatment for type 1 diabetes mellitus autoimmunity including (i) selecting a subject in need of a treatment for type 1 diabetes mellitus autoimmunity; and (ii) administering a therapeutically effective amount of the composition of any one of the compositions in accordance with the present invention to the subject. Selection of a patient in need of a treatment can include physical examination by a physician and/or laboratory tests.

In one embodiment, the composition is immunomodulatory. In one embodiment, the composition is not immunosupressive. In one embodiment, the composition elicits a Th2 immune response. In one embodiment, the composition does not elicit a Th1 immune response.

In one embodiment, the subject is a human adult. In another embodiment, the subject is a human juvenile.

In one embodiment, the subject has type 1 diabetes mellitus and the treatment achieves at least one clinical endpoint (e.g., improved C-peptide secretion, reduced insulin use, improved HbA1c, closer to normal blood sugar levels, less blood sugar level fluctuation and the like).

In one embodiment, the subject has type 1 diabetes mellitus and the treatment mitigates at least one symptom of the type 1 diabetes mellitus (e.g., frequency of hypoglycemia/hyperglycemia, reduced glucosuria, level/number of hospitalization, and level/number of complications such as nephropathy, neuropathy, and retinopathy).

In one embodiment, the subject has pre-clinical type 1 diabetes mellitus and the treatment prevents or delay progression to clinical type 1 diabetes mellitus.

In one embodiment, the subject is predisposed to developing type 1 diabetes mellitus and the treatment prevents or delays development of type 1 diabetes mellitus.

In one embodiment, the treatment mitigates autoimmunity to pancreatic beta cells.

In one embodiment, the administering step comprises intravenous, intramuscular, or subcutaneous administration.

In one embodiment, the method also includes determining if a subject is in need of a treatment for type 1 diabetes mellitus autoimmunity prior to administering the therapeutically effective amount of a therapeutic compound or composition in accordance with the present invention.

In one embodiment, a therapeutically effective amount can be 5 micrograms to 10 milligrams, 0.5 to 4.0 milligrams, or any value there between. In various embodiments, a therapeutically effective amount can be 5, 10, 25, 50, 75, 100, 125, 150, 175, 200, 225, 250, 275, 300, 350, 400, 450, 500, 600, 700, 800, or 900 micrograms, or any value there between. In various embodiments, a therapeutically effective amount can be 1.0, 1.25, 1.5, 1.75, 2.0, 2.25, 2.5, 2.75, 3.0, 3.25, 3.5, 3.75, 4.0, 4.25, 4.5, 4.75, 5.0, 5.5, 6.0, 6.5, 7.0, 7.5, 8.0, 8.5, 9.0, 9.5, or 10 milligrams, or any value there between. In various embodiment, a therapeutically effective amount can be determined by the detection of beneficial immune response (e.g., Th2/Treg response) and/or by the detection of at least one clinical endpoint or at least one symptom reduction (e.g., as discussed above).

In one embodiment, administration can include a depot injection. Administration can be in repeated intervals of about 6 months to 2 years. In various embodiments, the interval can be 1, 2, 3, 4, 5, 6, 7, 8, 9, 10, or 11 months, or 1, 2, 3, 4 years. In various embodiments, the interval can be quarterly, semi annually, or annually. In various embodiments, the interval can be determined by monitoring an immune-modulatory response (e.g., Th1/regulatory cells) and adjusting the treatment accordingly (e.g., re-dose when the T cell number/activity start to fall).

EXAMPLES

Example 1

Polypeptide Synthesis

Chemistry and Manufacturing Introduction: Overlapping preproinsulin 20 amino acid peptides are designed such that each of following peptides overlaps by 10 amino acids with the preceding peptide sequence. These peptides are made as a monocomponent HPLC (C18 column) purified peptides, synthesized in a protein-core laboratory on a Protein Synthesizer Model 433A from Applied Biosystems, using amino acid preparations from Peptide International. This is a standard solid-phase peptide synthesis (SPPS) procedure, which has the following main steps:

Chain Assembly.

The assembly strategy used in the protein synthesis is ABI (Applies Biosystem Inc.)-Fmoc/Thr. The Fmoc group protects the a-amino group of the amino acid. The peptide is assembled from the C-terminus towards the N-terminus with the α-carboxyl group of the starting amino acid attached to a solid support (resin). The resin used for assembly is polystyrene bead, an insoluble support with size of 400-1000 micron in diameter swelled after washing with NMP (N-methylpyrrolidone). The resin is preloaded with the first amino acid (Thr) from the C-terminus.

The first step in chain assembly is deprotection, or removal of the protecting group. The Fmoc protecting group is removed using 22% piperidine. Conductimetric feedback of carbamate salt formed via removal of Fmoc group with piperidine/NMP can be used to show the coupling efficacy.

After deprotection, the next amino acid is activated and coupled to the deprotected amino end of the growing peptide and forms the peptide bond. Activation of the incoming amino acid carboxyl group is achieved using HBTU/HOBt.

Between couplings, the column is washed with methanol and NMP (N-methylpyrrolidone), which swells the resin and washes out residues. The cycle is repeated until a peptide of a desired length is achieved.

Then wash the resin with DCM (dichloromethane), which removes NMP from the resin, followed by thoroughly washing the resin with highly volatile methanol, which is an easily removable solvent, and evaporation/drying.

Cleavage from the Resin and Removal of Side Chain Protecting Groups.

A cleavage mixture is prepared (0.75 g crystalline phenol+0.25 g ethanedithiol+0.5 ml thioanisol+0.5 ml deionized H2O+10 ml trifluoroaceticacid). The dried peptide-resin is incubated in cool flask in ice bath (10 ml mixture/100-150 mg peptide-resin) for 1.5 h. Then isolate the peptide from the reaction mixture by glass funnel filtration under high vacuum. Precipitate the peptide with cold methyl t-butyl ether (MTBE) and vacuum dry.

Purification Under Sterile Conditions.

This step is performed with reverse phase HPLC. Buffer A=0.1% trifluoroaceticacid (TFA) and buffer B=70% acetonitrile, 30% H2O, 0.09% trifluoroaceticacid (TFA). By using C18 column the elution of the sample is based upon hydrophobicity (hydrophilic sample elute earlier). The peak detection is performed by absorbance measurement of peptide bond at 214 nm and identified by mass spectrometry. The desired fraction is pooled in sterile vials and lyophilized, with a sample taken for AAA (amino acid analysis) analytical rpHPLC and Mass Spectrometry to confirm the sequence.

Example 2

Preproinsulin Polypeptide Vaccine Formulations

A. A preproinsulin polypeptide (3P) vaccine. The 3P immune modulatory vaccine is a combination of the water-soluble preproinsulin 20-aminoacid overlapping polypeptide mixture and incomplete Freund's adjuvant solution. The injections/emulsions (the final drug products) are prepared immediately before administration in a lamina-flow protected hood, under sterile condition by using high-pressure sterile syringes as a 50/50 (w/w) emulsion of human preproinsulin peptides mix solution (0.5ml) by mixing with Montanide ISA51 (0.5 ml) (Seppic Inc.).

B. A preproinsulin polypeptide (3P) vaccine. The 3P immune modulatory vaccine is a combination of the water-soluble preproinsulin 20-aminoacid overlapping polypeptide mixture and incomplete Freund's adjuvant solution. The injections/emulsions (e.g., the final drug product) are pre-prepared (e.g., in a manufacturing setting) and can have an extended expanded shelf life (e.g., years).

C. A preproinsulin polypeptide (3P) vaccine. The 3P immune modulatory vaccine is a combination of the water-soluble preproinsulin 20-aminoacid overlapping polypeptide mixture and incomplete Freund's adjuvant solution. The injections/emulsions (e.g., the final drug products) are prepared as a kit; the two main components (e.g., peptides and adjuvant) in different sealed compartments with a built in mechanism to prepare a fresh mix to be used within short period of time (e.g., days/weeks).

D. A preproinsulin polypeptide (3P) vaccine. The 3P immune modulatory vaccine is a combination of the water-soluble preproinsulin 20-aminoacid overlapping polypeptide mixture and incomplete Freund's adjuvant solution, where incomplete Freund's adjuvant solution is other than Montanide ISA51.

E. A preproinsulin polypeptide (3P) vaccine. The 3P immune modulatory vaccine is a combination of the water-soluble preproinsulin 20-aminoacid overlapping polypeptide mixture and an immunological adjuvant other than incomplete Freund's adjuvant solution (e.g., squalene; killed bacteria and toxoids; aluminum salts-alum/inorganic compounds etc. or liposomes, lipid based nanoparticles, nanoemulsion, nanogels, dendrimers or the like).

Example 3

Preproinsulin Polypeptide Vaccine Therapies

A. Administer a composition in accordance with the present invention to a subject (e.g., of any age and/or any disease duration) who has been diagnosed with type 1 diabetes (e.g., a clinical diagnosis+at least one positive type 1 diabetes specific autoantibodies such as IAA, GAD65, Ia2, Zn transporter8 or type 1 diabetes specific T cell marker positive).

B. Administer a composition in accordance with the present invention to a subject who does not have clinical diagnosis of type 1 diabetes, but has at least one positive type 1 diabetes specific autoantibodies (e.g., IAA, GAD65, Ia2, Zn transporter8) or type 1 diabetes specific T cell marker. The subject can have normal glucose status or impaired glucose tolerance tested by oral glucose tolerance test. Such subjects can be identified by family screening of patients with type 1 diabetes, or by screening a larger population.

The section headings used herein are for organizational purposes only and are not to be construed as limiting the subject matter described in any way.

While the applicant's teachings are described in conjunction with various embodiments, it is not intended that the applicant's teachings be limited to such embodiments. On the contrary, the applicant's teachings encompass various alternatives, modifications, and equivalents, as will be appreciated by those of skill in the art.

What is claimed is:

1. A composition comprising two or more overlapping fragments of SEQ ID NO:1, an adjuvant that includes an oil and an emulsifier, and a pharmaceutically acceptable carrier, wherein each of the two or more overlapping fragments comprises a preproinsulin epitope, and wherein the fragments are 8 to 25 amino acids in length and comprise a first polypeptide fragment and a second polypeptide fragment that overlap by 5 to 20 amino acids.

2. The composition of claim 1, wherein the fragments are 20 amino acids in length.

3. The composition of claim 1, wherein the fragments are 25, 24, 23, 22, 21, 20, 19, 18, 17, 16, 15, 14, 13, 12, 11, 10, 9 and/or 8 amino acids in length.

4. The composition of claim 1, wherein the first polypeptide fragment and the second polypeptide fragment overlap by 10 amino acids.

5. The composition of claim 1, wherein the first polypeptide fragment and the second polypeptide fragment overlap by 20, 19, 18, 17, 16, 15, 14, 13, 12, 11, 10, 9, 8, 7, 6, or 5 amino acids.

6. The composition of claim 1, wherein the fragments are 20 amino acids in length and the first polypeptide fragment and the second polypeptide fragment overlap by 10 amino acids.

7. The composition of claim 1, wherein the fragments are 20 amino acids in length and the first polypeptide fragment and the second polypeptide fragment overlap by 19, 18, 17, 16, 15, 14, 13, 12, 11, 10, 9, 8, 7, 6 or 5 amino acids.

8. The composition of claim 1, comprising 3, 4, 5, 6, 7, 8, 9, 10, 15, 20, 25, 30, 35, 40, 45, 50, 60, 70, 80, 90, 100 or more overlapping preproinsulin polypeptide fragments.

9. The composition of claim 1, wherein the pharmaceutically acceptable carrier comprises an incomplete Freund's adjuvant (IFA).

10. The composition of claim 1, wherein the pharmaceutically acceptable carrier comprises an alum adjuvant.

11. The composition of claim 1, further comprising one or more beta cell promoting agents, anti-inflammatory agents, and/or anti-autoimmunity agents.

* * * * *